United States Patent [19]

Busse et al.

[11] Patent Number: 4,582,950

[45] Date of Patent: Apr. 15, 1986

[54] REMOVAL OF ACETYLENE AND CARBON MONOXIDE FROM METHANE AND ETHANE

[75] Inventors: Paul J. Busse; Douglas B. Taggart, both of Omaha, Nebr.

[73] Assignee: InterNorth, Inc., Omaha, Nebr.

[21] Appl. No.: 682,556

[22] Filed: Dec. 17, 1984

[51] Int. Cl.$^4$ .................. C07C 7/00; C01B 31/18
[52] U.S. Cl. .................. 585/833; 585/868; 423/245; 423/246
[58] Field of Search .................. 585/868, 833; 423/245 DR, 245 S, 246

[56] References Cited

U.S. PATENT DOCUMENTS

| 1,908,312 | 5/1933 | Brittin et al. | 585/800 |
| 2,381,707 | 8/1945 | Wood | 423/245 |
| 3,233,004 | 2/1966 | Hirschbeck | 423/246 |
| 4,328,382 | 5/1982 | Alter | 585/844 |

FOREIGN PATENT DOCUMENTS 297842  8/1929  United Kingdom .

*Primary Examiner*—William R. Dixon, Jr.
*Assistant Examiner*—Cynthia A. Prezlock
*Attorney, Agent, or Firm*—Donald F. Haas

[57] ABSTRACT

A method is disclosed for the purification of methane and/or ethane which comprises oxidizing acetylene and/or carbon monoxide in the gas with oxygen at 200° C. to 375° C. in the presence of a catalyst which contains silver as the active component.

2 Claims, No Drawings

REMOVAL OF ACETYLENE AND CARBON MONOXIDE FROM METHANE AND ETHANE

BACKGROUND OF THE INVENTION

This invention describes a process for the removal or reduction in concentration of acetylene and carbon monoxide from methane and ethane. These impurities are typically found in methane and ethane that is derived from synthetic sources but may also be found in natural gas or in other gas mixtures.

These organic oxidizable impurities can be removed or reduced in concentration by a wide variety of chemical or physical procedures. Physical procedures for removal from methane are represented by distillation and adsorption. Both methods are based on equilibrium processes which require multiple steps for each additional increment of impurity removal. In addition, the physical methods generally are operated under cryogenic conditions which are comparatively costly. As a consequence, physical methods of impurity separation are terminated at an economic barrier depending on the economic advantage of removing an additional increment of impurity or at the desired methane/ethane purity level which may be beyond the economic barrier. It is particularly costly to purify methane or ethane beyond the economic barrier.

An alternative to physical methods of impurity removal from methane is the use of catalytic reduction. In this process, excess hydrogen is mixed with the impure methane stream which is then fed to a catalytic reactor in which certain of these impurities, such as olefins, may be converted to methane. This procedure does not extract the value of the impurities but does reduce their concentration. However, hydrogen is a relatively expensive material and is not always conveniently available.

In many cases the impurity level of methane and/or ethane may not affect its use and in some cases it may even be beneficial. However, in certain cases, it is important that the purity level of the methane and/or ethane be extremely high and the complete absence of these impurities is preferred. To accomplish this control of the impurity concentration via the extant physical or chemical procedures would be complicated and expensive or both. Thus it can be seen that there is a need for a less expensive method which is capable of reducing the concentration of these impurities in methane and/or ethane to very low levels.

SUMMARY OF THE INVENTION

The present invention provides a method of purification of methane and/or ethane which is based on oxidation of the impurities in the methane and/or ethane. The oxidizing agent is oxygen and the process is conducted in a catalytic reactor operating in the temperature range of 200° to 375° C. Catalysts effective for this process contain silver as the active component.

The process consists of mixing a sufficient quantity of oxygen with the methane and/or ethane stream to permit combustion of the contaminants. This stream is then passed through a catalyst bed providing the required conditions of oxidation. The resulting products of the purification step are carbon dioxide and water. These may be removed via conventional processes or left in the methane and/or ethane stream as desired.

DETAILED DESCRIPTION OF THE INVENTION

When an impure methane and/or ethane stream containing oxygen and optionally an inert gas such as nitrogen is passed over a catalyst as described below, combustion occurs predominantly among the contaminants before methane and/or ethane combustion occurs. With the catalysts described herein, the combustion process is normally very efficient providing carbon dioxide and water as the sole products. Control of the reaction can be achieved by controlling the variables of oxygen concentration, reactor temperature, and flow rate. By proper adjustment of these parameters, the impurities can be removed with little effect on the methane and/or ethane concentration. If the oxygen concentration required for complete removal of the impurities is higher than the flammability limit of the mixture, then a multiple-step process may be conducted in which oxygen is added to the methane and/or ethane stream at a safe concentration in each step until the desired impurity level is reached.

It goes without saying that for economic reasons it would be preferred to remove all of the contaminants in a one-step process if that is possible. The process of the present invention can be performed in one step if the concentrations of the contaminants are such that the oxygen concentration required to oxidize them is below the flammability limit of the gas mixtures so that the purification can take place without fear of an explosion. The methane and/or ethane stream and the oxygen are led to a catalytic reactor wherein the reaction temperature is controlled within the range of 200° to 375° C. If the temperature is below 200° C., then the reactivity is insufficient and if the temperature is above 375° C., then too much methane and/or ethane is oxidized. The oxygen concentration should be maintained at a level higher than but close to the stoichiometric concentration required to oxidize the contaminants. Preferably, the oxygen concentration range is from 0.5% to 1% above the stoichiometric concentration because more oxygen provides no benefit and would bring the mix closer to the flammability limit.

The amount of time that the gas mixture is in contact with the catalyst is also an important variable. The contact time can be increased by increasing the size of the reactor. It can also be increased by slowing down the flow rate of the gases through the reactor. The contact time is generally measured in terms of space velocity in units of hour$^{-1}$. Thus, it is preferred that the space velocity be in the range from about 50 to about 1,000 hour$^{-1}$, preferably for the most practical operation 100 to about 500 hour$^{-1}$, if the reaction takes place at atmospheric pressure because it allows maximum use of the reactor. Higher flow rates can be used if the temperature is increased.

In situations where the concentration or type of the impurities requires an oxygen concentration which is above the flammability limit of the gas mixture, multiple oxidation steps are required. Preferably, for safety and economic reasons, two oxidations take place. In each oxidation step, the concentration of the oxygen is kept below the flammability limit to prevent explosive combustion.

A wide variety of silver-based catalysts can be used to advantage in the present invention. These catalysts generally comprise a silver salt deposited on a porous support material such as alumina, silica or other inert refractory material. The catalyst might also include promoters such as alkali metals and alkaline earth metals. Commercially existing ethylene oxide silver-based catalysts generally provide acceptable performance in this process. Catalysts of this type are described in U.S. Pat. No. 3,725,307, issued Apr. 3, 1973.

The process may be operated with inert gases such as nitrogen or argon in the methane and/or ethane stream. The combustion products of the oxidation reaction are carbon dioxide and water and may be removed by conventional purification techniques if their presence is not desired in the purified methane and/or ethane stream. For use in an ethylene oxide reactor, the presence of carbon dioxide or water in the methane and/or ethane stream should not be detrimental to the process as both components are normally present in the reactor. If oxygen is not totally consumed in the purification process, the unreacted oxygen may be used to supplement the oxygen feed to the reactor.

The process is particularly suited for the removal of acetylene and carbon monoxide from methane, ethane, and methane and ethane gas mixtures. Carbon monoxide may be present in methane or ethane which is derived from synthetic natural gas plants or from refineries. It, as well as acetylene, can be removed according to this process.

EXAMPLE I

Removal of Acetylene and Carbon Monoxide from Methane

Acetylene and carbon monoxide may be present in methane derived from an ethylene cracker. Both components should preferably be removed from the methane before it is used as ballast gas in an ethylene oxide reactor. Oxidative purification can be applied to the purification of the methane stream.

Complete combustion of acetylene to carbon dioxide and water requires 2.5 volumes of oxygen per volume of acetylene whereas complete combustion of carbon monoxide to carbon dioxide requires 0.5 volumes of oxygen per volume of carbon monoxide. For enhanced efficiency of contaminant removal, an excess of oxygen may be added to the methane stream with from 0.5 to 1% normally being adequate for optimum removal.

If the concentration of contaminants requires an oxygen concentration greater than the flammability limits of the gas mixture, then a multiple pass process should be conducted in which oxygen is mixed with the methane stream to a concentration below the flammability limit. This mixture is passed through the catalytic reactor in which combustion of some of the impurities occurs. The resulting partially purified methane stream is again admixed with oxygen at a concentration below the flammability limit and reacted for a second time. This process is repeated until the concentration of impurities is down to the desired level.

A methane stream containing acetylene, 1000 ppm, and carbon monoxide, 2000 ppm, is mixed with oxygen to give an oxygen concentration of 0.75%. The oxygenated methane stream is fed to a reactor at a space velocity of 200 per hour and in the temperature range of 230°–240° C. The acetylene and carbon monoxide concentration of the outlet stream is greatly reduced.

We claim:

1. A method for removing carbon monoxide from methane, ethane and mixtures thereof, which comprises oxidizing the carbon monoxide in the gas with oxygen at 200° C. to 375° C. in the presence of a catalyst which contains silver as the active component wherein the concentration of the oxygen is below the flammability limit of the gas mixture.

2. The method of claim 1 wherein the oxygen concentration is slightly in excess of the stoichiometric concentration required to oxidize all of the impurities in the methane.

* * * * *